United States Patent [19]
Hill

[11] Patent Number: 4,993,949
[45] Date of Patent: Feb. 19, 1991

[54] METHOD FOR HANDLING SMALL OBJECTS

[76] Inventor: Sheryl L. Hill, 14830 SW. Farmington Rd., Beaverton, Oreg. 97007

[21] Appl. No.: 467,644

[22] Filed: Jan. 19, 1990

[51] Int. Cl.⁵ .............................................. A61C 3/00
[52] U.S. Cl. ...................................... 433/141; 433/229
[58] Field of Search ............... 433/141, 153, 163, 215, 433/229, 3

[56] References Cited

U.S. PATENT DOCUMENTS

| | | | |
|---|---|---|---|
| 3,797,875 | 3/1974 | den Hamer | 294/1 R |
| 3,974,539 | 8/1976 | Barouh et al. | 15/104 R |
| 4,073,530 | 2/1978 | Seidler | 294/19 R |
| 4,834,654 | 5/1989 | Nussbaum | 433/141 |

*Primary Examiner*—Cary E. Stone
*Assistant Examiner*—Michael Lynch
*Attorney, Agent, or Firm*—Chernoff, Vilhauer, McClung & Stenzel

[57] ABSTRACT

A tool and method for handling small objects particularly suitable for placing small cast restorations into prepared cavities inside the mouth of a dental patient. The tool comprises an elongate handle having an adhesive tip of nonhardening pliable adhesive material. The material is plastically deformable, upon sustained pressure, and a forward bonding surface may be formed of a size appropriate for the size of the object to be placed and the contour of the placement location. A lump of the material encompasses a terminal portion of the handle, and the tool is operable at any convenient angle within the space restrictions inherent at a particular location. Economical manufacture allows disposable use of the tool and lessens the likelihood of transferring infection between patients.

5 Claims, 2 Drawing Sheets 4,993,949

METHOD FOR HANDLING SMALL OBJECTS

BACKGROUND OF THE INVENTION

The present invention relates to a tool and method for placing small objects and particularly to a tool having an adhesive tip suitable for use in medical or dental procedures.

Various devices have been developed for holding and placing small objects during dental and medical procedures none with completely satisfactory results. Placement of objects is sometimes attempted through use of the physician's or dentist's gloved fingers, but this is clumsy, particularly when a small object must be aligned to fit in a particular position within a confined space. However, the gloves are disposable, thus reducing the risk of transferring infection.

Tweezers are sometimes employed, but again, because two opposed faces on the object are required for proper grasping, alignment is difficult; the object may inadvertently drop past a recessed location rather than in the location, and there is a significant risk that the object will be swallowed or aspirated if the object drops in the patient's throat. Furthermore, delicate items, such as thin porcelain veneers that are used to overlay a patient's natural teeth, are frequently broken when being handled by the use of tweezers.

The increasing presence of incurable diseases has caused heightened concern about the transfer of infection in the workplace, particularly in the medical or dental specialties where internal procedures may greatly increase the risk of transferring infection between patients. To aid in preventing such infections, medical and dental tools are routinely sterilized. The tools must be collected after each use, sterilized in an autoclave or similar device, and then sorted and replaced so that each storage cabinet has a full set of tools. Valuable staff time is consumed during such procedures and it is desirable to minimize the number of tools requiring such treatment.

Convenient manipulation of small objects is provided by specialized holding tools having adhesive tips that require only one available face of the object to achieve proper gripping. The remaining faces of the object are then engageable with the walls of the location before the object has been released from the tool, thereby preventing inadvertent dropping.

As disclosed in Seidler U.S. Pat. No. 4,073,530, one type of such tool relies on an elastic adhesive tip having a flat or slightly projecting forward bonding surface with angular shoulders. During release of the object from the tool, the elastic adhesive snaps away from the object as the forward bonding surface is rolled along the object towards the angular shoulders. To ensure that the forward bonding surface is level in relation to the placed object, when the handle is at a convenient angle in the patient's mouth, an angular bend may be provided in the handle, or the tip end may be oriented at an angle to the handle. Because several objects might require placement at several different locations inside an individual patient's mouth, it is advantageous to have on hand a variety of such tools, having bends in their handles or tips oriented at a variety of angles, to obtain the most convenient angle of access into the mouth for that location. It is also convenient that such tools be equipped with a variety of tip sizes. While large tip ends, providing large forward bonding surfaces, are useful for larger or heavier items, smaller bonding surfaces are needed for smaller items where overhanging tip surfaces would hide a small object or impede its progress into a recessed location. Such variety of tools, however, increases the time associated with sterilization procedures and with tool selection. Furthermore, it is difficult to apply heat to such elastic tips, for the purpose of sterilization, without stiffening, cracking, or degrading the bonding strength of the tip. Washing at cooler temperatures is possible, but does not ensure the absence of contamination.

An alternative type of holding tool relies on a rigid adhesive stick. Rather than attempting sterilization of the adhesive tip, the used portion of the rigid stick may be broken off and the newly exposed portion of the stick may be shifted into appropriate position by sliding the stick down a hollow chamber in the handle. Such an arrangement is disclosed in den Hamer U.S. Pat. No. 3,797,875. The rigidity of the stick, however, increases the likelihood that breakage will occur to delicate objects as the stick is pressed against such objects to establish a bond. Furthermore, as was true with tools using elastic tips, to reach a variety of internal locations with objects of varying size one may require a number of such tools having varying handle shapes and tip sizes, thereby increasing the time expended for sterilization and tool selection. Specific adhesive materials that have been identified for use with holding tools include silicone-based materials providing elastic tips, as described in Seidler where the tip reverts quickly back to its original shape after deformation. Synthetic rubbery adhesives have been used to provide solid stick-like tips as described in den Hamer. Brittle stick-like adhesive tips have been formed from beeswax, as described in den Hamer, or a mixture of paraffin and petroleum wax, as described in Barouh et al., U.S. Pat. No. 3,974,539. Attempts have been made to adapt various types of sealing adhesives or softer waxes for use as a tip material for similar tools, but sealants harden rapidly into a rigid unworkable condition and softer waxes have generally been found to lose their stickiness after only a brief period of manipulation. Conventional flexible adhesive tapes appear to maintain their stickiness with use, but frequently such materials do not release easily from the object and often leave a sticky film thereon that requires alcohol or other hazardous solvents for removal.

What is needed, then, is a more practical tool, and a method for its use in sterile conditions, for handling small objects and precisely placing such objects at locations internal to a patient.

SUMMARY OF THE PRESENT INVENTION

The present invention overcomes the aforementioned shortcomings of previously available tools, by providing a disposable tool including a handle whereon an adhesive tip is mounted, such adhesive tip being made of a pliant nonhardening material. An exemplary embodiment of the present invention provides an adhesive tip on an elongate handle, where the tip comprises an integral lump of plastically deformable nonhardening adhesive material. Because the adhesive material is plastically deformable with moderate pressure, it can be shaped to provide a forward bonding surface of a selected size, thereby permitting a single tool to be adapted to handle objects of widely varied size for placement at many different types of locations.

The preferred plastically deformable adhesive presents a minimum risk of breakage of a fragile object such as an artificial inlay for a tooth, and absorbs the powder in which dental gloves are packed to prevent them from sticking together, while retaining its bond strength. At the same time, a preferred nonhardening adhesive is not susceptible to the cross-linking or dehydration typically occurring in rubbery or water-permeable adhesives, thereby permitting an extensive shelf life.

Because the adhesive material surrounds a terminal portion of the handle, the forward bonding surface may be established at a wide range of angles relative to the handle, thereby permitting a single tool to be used at any attainable angle convenient to an internal location. Low cost of the tool of the invention makes disposal after a single use economical and thus lessens the risk of transferring infection.

Accordingly, it is a principal object of the present invention to provide an improved adhesive-tipped tool and method for its use for placing small items inside a patient.

A further object of the present invention is to provide an improved tool and method for successively placing several small items at respective locations inside a patient without requiring multiple tools.

Yet a further object of the present invention is to provide a tool having a moldable adhesive tip for deposit of small items internal to a patient at locations where there are varying degrees of clearance.

Still another object of the present invention is to provide a tool having a conveniently moldable adhesive tip that maintains its plasticity over an extended shelf life.

A still further object of the present invention is to provide a holding tool having a nonhardening moldable adhesive tip for manipulating small fragile objects with a minimum of breakage.

An additional object of the present invention is to provide a tool for manipulation of small objects that has a moldable tip conveniently releasable from an object without leaving a sticky residual film thereon.

Still an additional object of the present invention is to provide a dental tool having a moldable adhesive tip which is nontoxic for use in a patient's mouth, nonreactive with restorative dental surfaces, and manipulable through powdered dental gloves without significant loss of bonding strength thereof.

The foregoing and other objects, features, and advantages of the present invention will be more readily understood upon consideration of the following detailed description of the invention, taken in conjunction with the accompanying drawings.

DETAILED DESCRIPTION OF THE DRAWINGS

Figure 1:
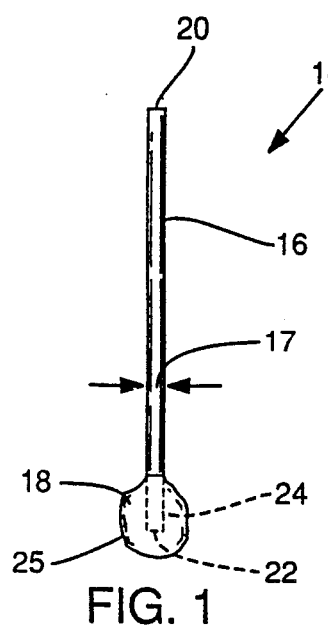
FIG. 1 is an enlarged front view of a small object placement tool which is an embodiment of the present invention.

Referring now to the drawings, FIG. 1 shows an exemplary small object placement tool 14 constructed in accordance with the present invention and suitable for the placement of small objects during internal procedures upon a patient. The tool is particularly useful for dental applications, where orthodontic brackets, crowns, porcelain veneers, and cast restorations generally, are required to be placed in a patient's mouth.

The tool 14 comprises an elongate handle 16 and a lump 18 of nonhardening adhesive material which is plastically deformable at ambient room temperatures, i.e., in the range of 65° F. to 80° F., and which preferably remains plastically deformable over a wider range of temperatures, i.e., 50° F. to 100° F., to permit operability under widely varying environmental conditions. The handle 16, for ease of manufacture, is preferably a straight cylindrical polymeric rod, cut, at its two ends 20 and 22, from a longer rod of uniform diameter. The handle 16 may be provided with a bent portion and with a varying longitudinal diameter but, to economize on forming costs, the handle 16 is preferably straight and of uniform diameter throughout its length. It will be recognized that inexpensive manufacture of the tool permits the tool to be sold as a disposable item. The diameter 17 of the handle 16 is preferably large enough to provide the required strength and for the tool to be lifted and held easily, yet small enough for the tool to be rotated readily between the user's fingers. A diameter in the range from 0.1 to 10.0 mm is appropriate, with a diameter in the range from 1.25 to 2.5 mm being preferred.

The lump 18 of adhesive material is mounted on the handle 16 at a terminal portion 24 thereof. As used in this specification, including the claims, the term "plastic" or "plastically" is intended to denote the quality of plasticity or inelasticity wherein the shape last attained by the material upon pressure deformation is maintained. Typically, the adhesive material used will be economically purchased in block-size quantities and smaller pieces will be removed from the block. The terminal portion 24 of an individual handle 16 may then be inserted into each of these smaller pieces. It has been found convenient to provide enough adhesive material on the handle 16 so that a ball of adhesive may be formed at least as large as three times the diameter 17 of the handle.

Figure 2:
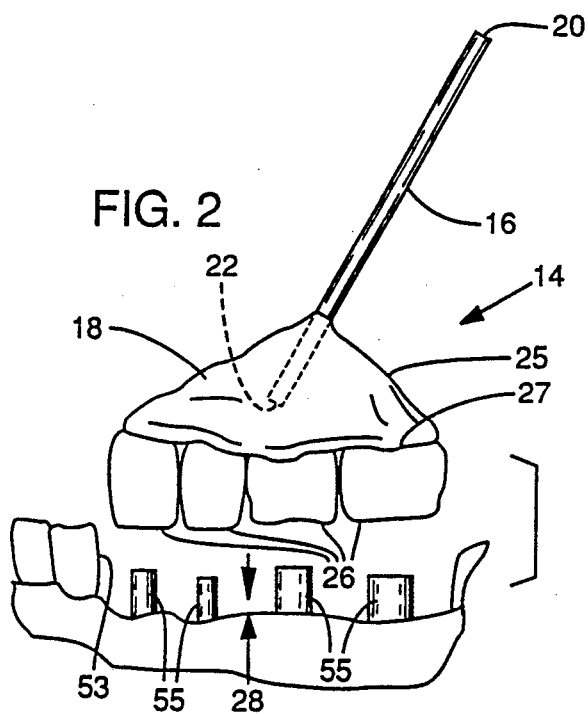
FIG. 2 is an enlarged front view of the tool of FIG. 1 to which additional adhesive material has been added for the placement of multiple objects, such objects here being represented as a group of artificial teeth.

The lump 18 of plastically deformable nonhardening adhesive material has an outer bonding surface 25. As suggested by FIG. 2, this outer bonding surface 25 may be increased in area by pinching off the lumps 18 of adhesive material from several separate handles 16 and combining them onto a single handle 16. In this manner, as shown in FIG. 2, it is possible to position much larger objects or several objects such as crowns 26 at one time.

Figure 3:
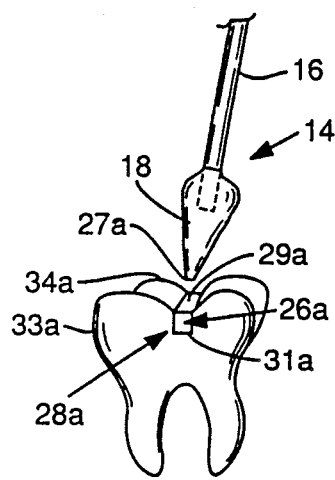
FIG. 3 is a perspective view of the tool shown in FIG. 1 with the plastic adhesive material molded to provide a forward bonding surface of an appropriate size for placement of an object at a recessed location.
Figure 4:
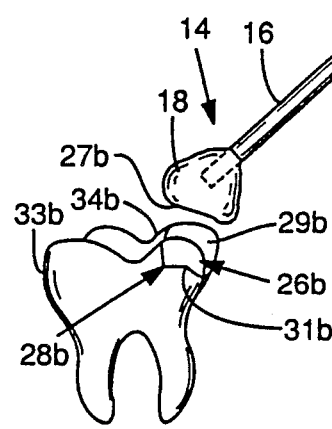
FIG. 4 is a perspective view of the tool shown in FIG. 1 with the plastic adhesive material molded to provide a forward bonding surface of an appropriate size for placement of an object at a projecting location.

The particular portion of the outer bonding surface 25 of the adhesive lump 18 which is placed into adhesive contact with an object to be moved will be referred to as the forward bonding surface, and is labeled by reference number 27 in the drawings. Because the adhesive lump 18 is plastically deformable, the size of the forward bonding surface is selectable and may be made smaller or larger than the diameter of the handle 16, depending on the size of the objects to be moved and the contour of the location 28 at which the objects 26 are eventually to be seated. As shown in FIGS. 3 and 4, the size selected for the forward bonding surface 27a or 27b can be varied to fit on, or engage, only the available surface area 29a or 29b of either a smaller filling 26a or a larger filling 26b without engaging the nonavailable surface area 31a or 31b of these same objects. The nonavailable surface area of an object or objects is that portion of the object or objects eventually coming to rest in contact with the tooth or other material defining the location at which the object is seated. In FIG. 3, the filling 26a requires placement at a recessed location 28a wherein the top or occlusal surface 34a of the tooth 33a slopes upwardly from the top or occlusal surface of the filling 26a. To seat the filling 26a properly, then, no portion of the forward bonding surface 27a should, after engagement of the filling 26a, project beyond the available surface area 29a. In FIG. 4, in contrast, the filling 26b requires placement at a projecting location 28b wherein the top or occlusal surface 34b of the tooth 33b slopes downwardly from the top or occlusal surface of the filling 26b. Here, as shown in FIG. 4, the forward bonding surface 27b may, during engagement, project beyond the available surface area 29b of the object as long as the forward bonding surface 27b does not extend along the nonavailable surface area 31b.

After the appropriate size of the forward bonding surface 27 has been determined by evaluation of the available surface area of the object to be moved or held by the tool 14 of the invention, and the contour of the placement location, the lump 18 of adhesive may be manually fashioned by squeezing the lump 18 of adhesive material into a suitable shape for providing a forward bonding surface 27 of the determined size. The forwardly tapering conical shape and rearwardly tapering conical shape depicted in FIGS. 3 and 4, respectively, are representative of the many available possibilities. Shaping the lump 18 of adhesive material requires that the adhesive material be easily plastically deformable, at ambient temperatures, so as to retain its last shape rather than elastically resume its former shape. Brittle adhesives which break up or flake during attempted molding at ambient temperatures, and elastic adhesives which do not retain a manually-molded shape, are unsuitable.

Figure 5A:
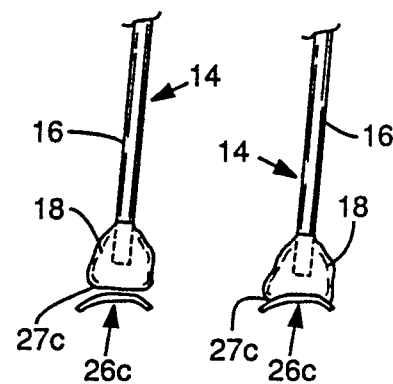
FIGS. 5a and 5b are views of the tool shown in FIG. 1 just before, and just after, engagement with a thin, curved, brittle porcelain veneer.
Figure 5B:
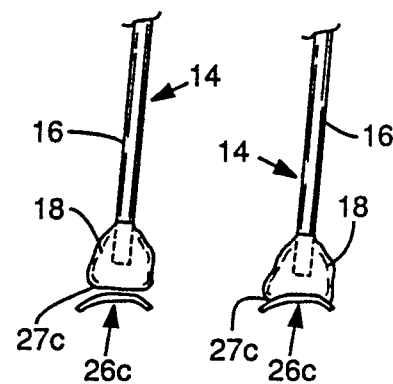

After being formed, the forward bonding surface is applied against the object to be carried, such as a filling 26a, with sufficient force and for a sufficient time to adhesively engage the object. Drying the object before applying the forward bonding surface to the object can facilitate adhesion. Further manipulation and placement of the object can then be achieved by manipulation of the handle 16. Because the adhesive lump 18 is plastically deformable at ambient room temperatures, the forward bonding surface of the adhesive lump 18 will have a tendency to plastically deform, that is, to conform partially to the surfaces of curved objects, during engagement of the lump to the curved object. This is illustrated in FIGS. 5a and 5b where the forward bonding surface 27c of the adhesive lump 18 is seen to have adopted the curved profile of the thin porcelain veneer 26c, as downward pressure is gradually applied by the handle 16 through the adhesive lump against the porcelain veneer 26c. Such conforming plasticity reduces the likelihood that the expensive porcelain veneer 26c will crack or shatter during engagement.

An adhesive material chosen for the lump 18 of the tool 14 of the present invention should retain its plasticity over time and upon exposure to the ambient air, that is, should be nonhardening. If the adhesive lump 18 were to harden, the forward bonding surface 27 of the adhesive would no longer be formable in size nor partially conformable to the exterior of an object upon engagement. It is particularly important, consistent with economical packaging and sale of the tool as a disposable item, that hardening of the lump 18 of adhesive material not occur upon exposure to air over a normal shelf life for the tool, a period of time that can extend over several months or more. The tool 14 may then be conveniently packaged inside thin-film polymer bags. Unlike rubbery adhesives, the adhesive material of the lump 18 should not be susceptible to cross-linking and stiffening; nor should the adhesive material be of a type that hardens within minutes after removal from its package as is typical of cement-like adhesives which quickly dry out to a brittle condition.

Other desirable properties of the adhesive lump 18 include dryness, so that no oily film is left on the object after disengagement, and nonabsorbency of water, so that the material retains its adhesive character in a wet environment. The adhesive material is preferably tacky, but not overly sticky, so as to separate cleanly from an object. More particularly, the cohesiveness of the lump 18 of adhesive material should be greater than its ability to adhere to a smooth, nonporous, rigid surface, such as a dental filling 26b, so that the adhesive material of the lump 18 separates cohesively from such an object leaving substantially none of itself apparent on the surface thereof. A preferred adhesive material for the lump 18 having the requisite viscosity, tackiness, and nonhardening quality is a proprietary composition obtainable from Yaley Enterprises, P.O. Box 2225, 145 Sylvester Road, South San Francisco, Calif. under the supplier's designation, as "Rope Caulk RV3024-2."

Analysis of the chemical composition of this proprietary material, by infrared spectroscopy and scanning electron microscopy-energy dispersive spectrometry (SEM-EDS), showed the presence of hydrocarbons, calcium carbonate and talc with approximately two times more calcium carbonate than talc. Extraction with dichloromethane indicated a 25% (wt) hydrocarbon content where the extracted hydrocarbon was a low melting-temperature wax with a consistency similar to petrolatum. From this analysis, this material appears to consist essentially of 25% (wt) hydrocarbon wax, 50% (wt) calcium carbonate and 25% (wt) talc. The plastically deformable nature of this adhesive material is in sharp contrast to the relative elasticity of prior art silicone-based adhesives, probably due to the kinking- and entangling-type bonding that is characteristic of such silicone-based adhesives.

The physical properties of caulking compound RV3024-2 were also analyzed. In relation to cohesiveness, the material was found to have a tensile strength of approximately 60,000 pascals, as measured with a cylinder of the material of 4.5 mm diameter where a 100 grams weight pulling on such cylinder caused breakage in approximately 30 seconds. In relation to bonding ability, the material was found to have an adhesive strength of approximately 27,000 pascals, as measured with a cone-shaped mass of material on an applicator stick pressed onto a porcelain surface. A maximum pulling weight of 94 grams with a contact area on the porcelain of 0.35 cm$^2$ was required to separate the material from the porcelain.

An alternative, but less desirable material, is red boxing wax as may be purchased from Kerr Manufacturing Co. of Romulus, Mich., catalog No. 48174. This wax is very sensitive to heat so storage and shipping restrictions would be necessary to prevent the wax from becoming too hot or too cold. As with other waxes examined, this wax cannot be manipulated for very long before it loses its tackiness.

Figure 6:
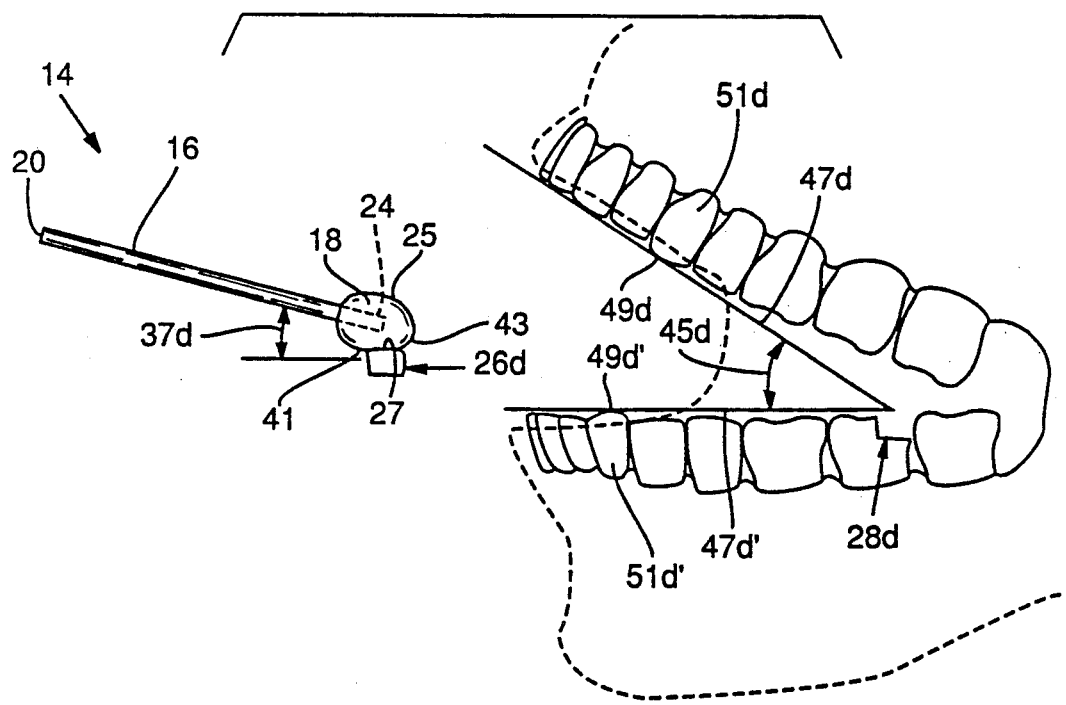
FIG. 6 is a schematic side view of a dental patient's open mouth and a tool of the type shown in FIG. 1 employed in accordance with the present invention, where the tool has been positioned for carrying a small dental filling to a rearward placement location in a patient's open mouth.
Figure 7:
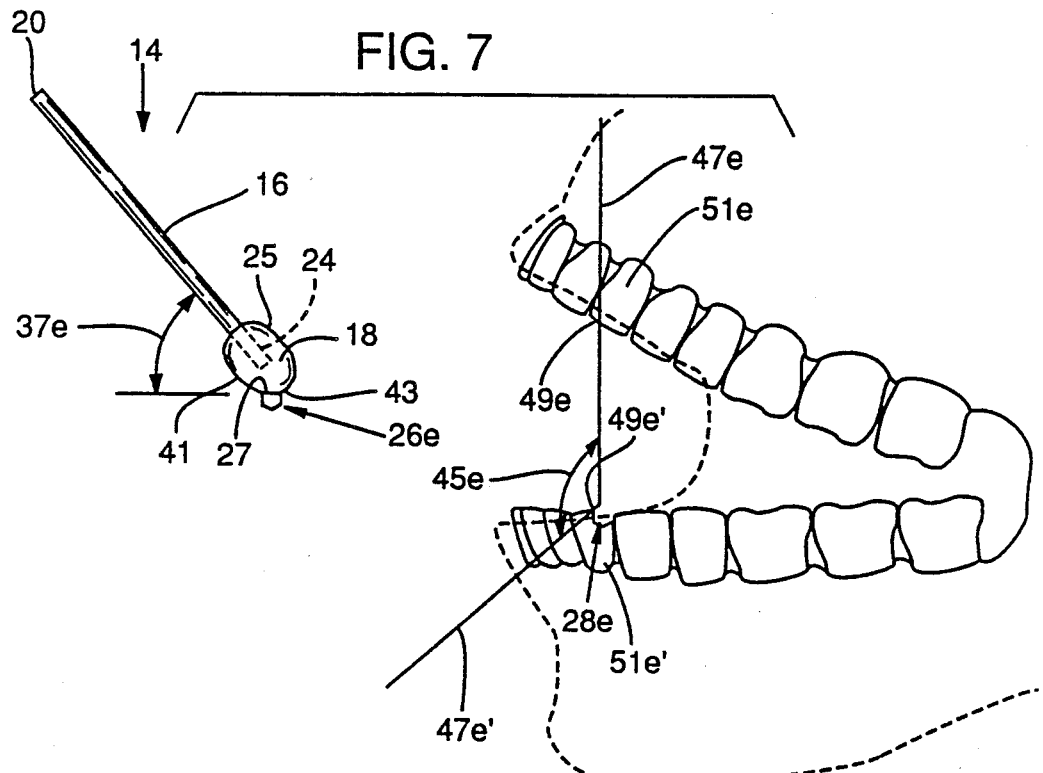
FIG. 7 is a view similar to FIG. 6, showing a tool of the type shown in FIG. 1 positioned for use in carrying a dental filling to a placement location in a forward portion of the patient's fully open mouth.

In FIGS. 3 and 4 the forward bonding surface 27 is substantially normal to the longitudinal axis of the handle 16. However, as shown in FIGS. 6 and 7, a forward bonding surface 27 may be selected on the outer bonding surface 25 so as to define, upon engagement, any one of a variety of angles 37d or 37e with the longitudinal axis of the handle 16. The angle 37d or 37e, formed upon engagement of the forward bonding surface 27 to the object 26d or 26e is called the angle of adherence, and is hereafter denoted generally by reference number 37. More particularly, the angle of adherence 37 is the smallest angle defined between an imaginary tangential plane to the outer bonding surface 25 at the forward bonding surface 27 adhered to an object and the longitudinal axis of the straight terminal portion 24. It will be seen that a site 41 may be selected on the outer bonding surface 25 so that the angle of adherence 37 is reduced to zero. This lower limit may be realized because the adhesive lump 18 surrounds or encompasses the straight terminal portion 24, that is, the outer bonding surface 25 includes a site 41 extending beyond, and having a tangent parallel to, the longitudinal axis of the terminal portion. It will also be seen that a site 43 may be selected on the outer bonding surface 25 so that the angle of adherence 37 attains 90°, this being the maximum angle of adherence 37. Although a variety of angles of adherence are available, the smaller angles, such as the angle 37d illustrated in FIG. 6, are generally most convenient when objects, such as a cast restoration 26d, are required to be placed at locations such as a cavity 28d near the posterior part of the mouth; the larger angles, such as the angle of adherence 37e illustrated in FIG. 7, are generally most convenient when objects, such as a cast restoration 26e, are to be placed at locations such as a cavity 28e near the forward part of the mouth.

At any particular location inside a patient's mouth there is a maximum angle of access defined by, for example, the teeth, gums or the cheeks, that sets an upper limit on the angle of adherence 37 usable for that location. As shown in FIG. 6 and 7, the particular maximum angle of access 45d or 45e is determined by the maximum angle obtainable between a pair of imaginary lines 47d and 47d' or 47e and 47e', each line intersecting the predetermined location, such as cavities 28d or 28e, and each line extending out of the patient's mouth while tangentially intersecting the outer margin of a respective oral structure, such as the occlusal surface 49d and 49d' or 49e and 49e' of a respective tooth 51d and 51d' or 51e and 51e'. As shown in FIGS. 6 and 7 as viewed together, it is not necessary that the proper pair of lines 47d and 47d' for one location 28d lie in the same plane as the proper pair of lines 47e and 47e' for another location 28e.

After a practitioner has examined the patient's fully opened mouth and determined the maximum angle of access 45 for a particular location 28 inside that mouth, she may then select any convenient forward bonding surface 27 on the outer bonding surface 25 of the adhesive lump 18 providing an angle of adherence 37 smaller than the maximum angle of access 45. This flexibility is achieved without having an angular bend in the handle and without a time-consuming search for the most suitably bent tool among the several that could clutter the equipment cabinet. The tool 14 disclosed herein permits use of the most convenient angle for a particular location inside the patient and may be discarded after treatment of that patient. The need for sorting out separate sets of angled tools, after sterilization procedures have been performed, is eliminated.

After the adhesive lump 18 has been pressed against the object or objects, and the objects have been manipulated into proper position at a predetermined location and, in most instances, have been secured in the required location by an appropriate seating adhesive which does not form a part of the present invention, then the forward bonding surface 27 must be disengaged or released from the objects. Referring again to FIG. 2, in some instances, release may be accomplished by rapidly levering end 20 of the handle 16 to describe an arc about handle end 22 proximate the crowns 26. The seating adhesive, the user's gloved fingers, or a second, nonadhesive tool may assist in holding the crowns 26 in place at the predetermined location, such as the cavity 28, while the forward bonding surface 27 is being disengaged from the crowns 26. In other instances, a sudden twist of the handle 16 about its longitudinal axis, combined with a simultaneous transverse pull towards an existing ledge 53 may be the most effective way of disengaging the tool 14 from the crowns 26. In most dental applications, as well as many medical situations, smooth restorative surfaces are desirable; so there are relatively few instances where angular objects are simply deposited on top of smooth, level locations where surrounding ledges are absent. Furthermore, as shown in FIG. 2, where the surfaces of the respective teeth 55 requiring restoration have been formed, by a grinding implement, into a pillar-like shape for engagement within a central cavity (not shown) in each respective crown 26, there are frequently prepositioned support members that will assist in retaining a crown or filling in place during disengagement of the tool 14. The existence of ledges or supporting members frequently facilitates removal of the adhesive material of lump 18 from medical or dental objects, thereby making it unnecessary to provide rigid or semi-rigid angular shoulders on lump 18 such as could be required, for example, if it were necessary that adhesive lump 18 be releasable, without manual assistance, from a flat semiconductive die positioned on a level electronic wafer.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method for placing an object in a predetermined location inside a dental patient's mouth, comprising:
   (a) providing an elongate handle having a straight terminal portion, said straight terminal portion being surrounded by a lump of plastically deformable nonhardening adhesive material;
   (b) shaping said adhesive material to form a forward bonding surface that fits within the available surface area of said object requiring placement, while being of sufficient size to adhere to and lift said object;
   (c) thereafter pressing said forward bonding surface against said object with sufficient force and for a sufficient time to attach said object thereto; and
   (d) manipulating said handle so as to place said object in a predetermined location inside the patient's mouth.

2. The method of claim 1 wherein said step of shaping includes shaping said adhesive material into a forwardly tapering conical shape for attachment to an object having an available surface smaller than the diameter of said terminal portion of said handle.

3. The method of claim 1 wherein said step of shaping includes shaping said adhesive material into a rearwardly tapering conical shape for attachment to an object having an available surface larger than the diameter of said terminal portion of said handle.

4. The method of claim 1, further comprising the steps of holding said object in place at said predetermined location and disengaging said forward bonding surface from said object.

5. A method for placing an object inside a dental patient's mouth at a predetermined location comprising:
   (a) providing an elongate handle having a straight terminal portion, said straight terminal portion being surrounded by a lump of deformable nonhardening adhesive material, said lump defining an outer bonding surface;
   (b) examining the patient's fully opened mouth to determine the maximum angle of access for said predetermined location;
   (c) thereafter shaping said outer bonding surface to provide a forward bonding surface thereon, such forward bonding surface defining with the longitudinal axis of the straight terminal portion an angle of adherence smaller than said maximum angle of access;
   (d) thereafter pressing said forward bonding surface against said object until said object is adhered to by said forward bonding surface to said handle; and
   (e) thereafter manipulating said handle so as to place said object at said predetermined location inside the patient's mouth.

* * * * *

UNITED STATES PATENT AND TRADEMARK OFFICE
CERTIFICATE OF CORRECTION

PATENT NO.   :   4,993,949

DATED        :   Feb. 19, 1991

INVENTOR(S)  :   Sheryl L. Hill

It is certified that error appears in the above-identified patent and that said Letters Patent is hereby corrected as shown below:

Column 4, lines 18, change "DRAWINGS" to --INVENTION--.

Signed and Sealed this

Twenty-second Day of September, 1992

Attest:

DOUGLAS B. COMER

*Attesting Officer*  *Acting Commissioner of Patents and Trademarks*